United States Patent [19]

Naftulin

[11] 4,129,131

[45] Dec. 12, 1978

[54] METHOD AND APPARATUS FOR DEFIBRINATION OF BLOOD

[76] Inventor: Henry Naftulin, 8341 N. Kenton Ave., Skokie, Ill. 60076

[21] Appl. No.: 735,173

[22] Filed: Oct. 26, 1976

[51] Int. Cl.² ............................................. A61M 1/03
[52] U.S. Cl. ..................................... 128/276; 422/44; 128/276–278, 214 A, 214 E, 214.2, 272, 275, 2 F, DIG. 5, DIG. 22; 23/258.5 R; 210/DIG. 23
[58] Field of Search .......... 128/214 R, 214 B, 214 D, 128/276–278, 214 A, 214 E, 214.2, 272, 275, 2 F, DIG. 5, DIG. 22

[56] References Cited

U.S. PATENT DOCUMENTS

| | | | |
|---|---|---|---|
| 1,614,337 | 1/1927 | Atwood | 426/422 |
| 1,973,990 | 9/1934 | Marrinan | 128/276 |
| 2,682,268 | 6/1954 | Ryan et al. | 128/214 R |
| 3,492,396 | 1/1970 | Dalton et al. | 128/214 R |
| 3,593,854 | 7/1971 | Swank | 210/DIG. 23 |
| 3,814,258 | 6/1974 | Ayres | 210/DIG. 23 |
| 3,986,506 | 10/1976 | Garber et al. | 128/272 |
| 4,014,329 | 3/1977 | Welch et al. | 128/276 |

OTHER PUBLICATIONS

Eisenman, Anna J. Method for Anaerobic Defibrination of Blood, J. Biol Chem., 71, 607–609 (1927).

Primary Examiner—William E. Kamm
Assistant Examiner—Jerome D. Stremcha
Attorney, Agent, or Firm—Joel E. Siegel

[57] ABSTRACT

A method and apparatus for collecting and defibrinating blood in a flexible container. The blood is collected in a flexible container of appropriate size into which is placed a sufficient quantity of glass beads or the like and a predetermined amount of gas. The flexible container is positioned within a vacuum chamber. The vacuum drawn in the chamber expands the gas within the flexible container to permit only about one half of the container to fill with blood. The flexible container is agitated causing the glass beads or the like to move rapidly through the blood and whip out the fibrin. An alternative embodiment substitutes a reticulated material in place of the glass beads positioned within the container.

10 Claims, 2 Drawing Figures

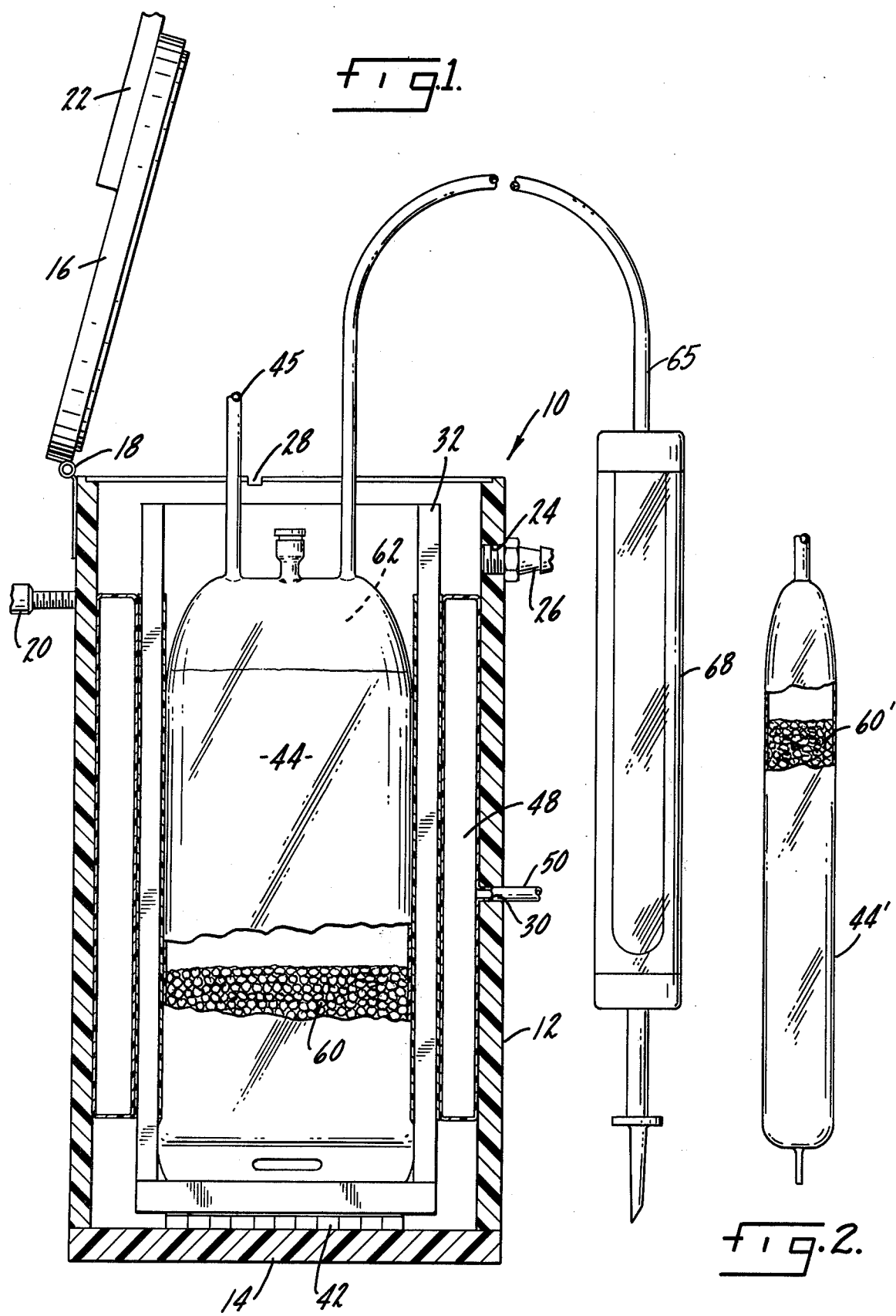

METHOD AND APPARATUS FOR DEFIBRINATION OF BLOOD

BACKGROUND OF THE INVENTION

This invention relates to a method and apparatus for the collection and defibrination of blood in flexible containers.

It is well known that is is necessary to take action either during or immediately after the collection of blood to prevent clotting of the blood. One such ction is the addition of anticoagulant drugs or chemicals to the blood. While the addition of these additives is effective to prevent the blood from clotting, there are instances where blood containing these additives may not be used; i.e., in the preparation of blood agar plates used in microbiology. In such instances it is necessary to defibrinate the blood. The term defibrination refers to a method to prevent blood from clotting after it is withdrawn from the donor without the addition of any chemical additives to the blood.

One procedure heretofore used to defibrinate blood utilizes beaters to whip the blood and thereby remove the fibrin necessary for clotting. Another heretofore used procedure utilizes a glass or other rigid material container to collect the blood. A sufficient amount of glass beads, marbles, metallic balls, or other formed elements or the like are placed in the rigid container. As the blood is being drawn into the container, the container is continuously shaken in a manner which agitates the glass beads or substitutes through the blood for a specified time sufficient to whip out the fibrin. In order to obtain the necessary whipping action of the beads within the blood, the container can only be about half full of blood. The reason for this is that the beads will move sluggishly through a container full of blood, but will move rapidly through a container half full of blood. This movement of the beads is most important since the speed of defibrination is essential if clotting is to be prevented.

While the above method of defibrination when performed properly prevents the clotting of the blood it has two serious drawbacks. Firstly, it requires the use of glass or other rigid material bottles and glass beads or the like. The bottles and beads must be sterilized for additional reuse. Such sterilization procedures are not only costly and time-consuming, but sometimes results in cross-contamination. Moreover, the use of glass bottles has often been found to be somewhat of a hazard, due to breakage and dripping problems. In other applications glass bottles have been replaced by flexible, disposable plastic containers. However, since the side walls of a half full flexible container collapse around the contained fluid, by merely substituting a flexible container for the glass bottle it has heretofore not been possible to attain the necessary movement of the beads through the collected blood. Secondly, the rigid container can only be approximately half filled with blood. This results in either the increase in bottle size or the use of additional bottles to collect a fixed amount of blood.

SUMMARY OF THE INVENTION

It is a primary object of the present invention to provide a method and apparatus for collecting and defibrinating blood in a flexible container.

A further object is to provide a method and apparatus for collecting and defibrinating blood in a flexible container without the use of glass beads or the like.

A still further object is to provide a method and apparatus for collecting and defibrinating blood in disposable flexible containers.

In accordance with the present invention the blood is collected in a flexible container of appropriate size into which is placed a sufficient quantity of glass beads or the like and a predetermined amount of gas. The flexible container is positioned within a rigid or semi-rigid inner chamber of proper height and diameter which is in turn positioned within an outer vacuum chamber. A vacuum of sufficient magnitude is drawn in the outer chamber to expand the gas within the flexible container to allow only approximately one half of the flexible container to fill with blood upon performing of the phlebotomy. The flexible container is sufficiently agitated causing the glass beads or the like to move rapidly through the blood and whip out the fibrin.

The present invention also provides an alternative flexible container for use in a similar manner as above which substitutes a reticulated material in place of the glass beads positioned within the container. This alternative container may be disposed of after each use.

BRIEF DESCRIPTION OF THE DRAWINGS

These and other objects and advantages of the invention will become apparent from the following description when taken in connection with the accompanying drawings. In the drawings, wherein like reference numbers have been used to designate like parts throughout:

FIG. 1 is a vertical sectional view of the apparatus constructed in accordance with a preferred embodiment of the invention; and FIG. 2 is a vertical sectional view of an alternative flexible container which may be substituted for the container shown in FIG. 1.

DESCRIPTION OF PREFERRED EMBODIMENTS

The present invention is hereinbelow described as used in combination with a presently preferred blood collection system of the type disclosed in U.S. patent application Ser. No. 735,764, and now U.s. Pat. No. 4,060,107 filed concurrently herewith and having the same inventive entity. The disclosure of said patent application is hereby incorporated by reference for the purpose of providing minor structural details which may not be fully apparent from the description contained herein. For the purpose of facilitating such reference, like reference numerals have been used to designate like parts. The disclosure of the present invention in combination with a specific blood collection system should not be construed as meaning that the teachings of the present invention are limited to the use with a particular blood collection system.

Refering to FIG. 1, there is shown a blood collecting apparatus indicated generally at 10. Apparatus 10 includes an outer chamber 12 of rigid construction. Chamber 12 is cylindrically shaped and closed at one end by a bottom portion 14. A top lid 16 is pivotally secured to the outer wall of chamber 12 adjacent its upper end through hinge member 18. Lid 16 is designed to pivot between an open position, as shown in FIG. 1, and a closed position in covering relationship to chamber 12. A stop member 20 is secured to chamber 12 to support the lid in its open position. A handle 22 is secured to lid 16. An opening 24 is provided through an upper portion of chamber 12 for receipt of a tapered fitting 26 therein. Fitting 26 is adapted to be connected to a vacuum line (not shown). An opening 28 is formed adjacent the upper periphery of chamber 12 to permit the blood collection line 45 to pass therethrough. An opening 30 is also provided through an intermediate portion of chamber 12 for receipt of a bladder line 50 therethrough. Openings 28 and 30 are sized in relationship to lines 45 and 50 so that a vacuum can be maintained in chamber 12.

A split inner chamber 32 is positioned within chamber 12. Chamber 32 is constructed of two opposing half cylindrical members pivotally secured together by hinge member 42. The half cylindrical members are pivotable between a closed position with the members in contact with each other and an open position with the half cylindrical members pivoted away from each other so as to effect an increase in the volume of inner chamber 32.

A flexible bladder member 48 is positioned within outer chamber 12 around inner chamber 32. Bladder 48 includes a bladder line 50 having one in communication with the interior of bladder 48 and the other end passing through opening 30 in chamber 12 for communication with the atmosphere. The interior of bladder 48 is thus in communication with the atmosphere through line 50.

Positioned within inner chamber 32 is a blood collecting flexible container or bag 44. The design of container 44 forms a very significant part of the invention. The skin portion of container 44 is of conventional construction and may be made from many flexible materials well known in the art, the most commonly used type being manufactured from a plastic material such as a polyvinylchloride resin base material. Container 44 includes a blood collection line 45 having one end in communication with the interior of container 44 and the other end extending through opening 28 for receipt of the collected blood thereinto. A sufficient quantity of glass beads, marbles, metallic balls, or formed elements or the like, indicated at 60, are disposed within container 44. Container 44 at atmospheric pressure is preferably about 30% full with the glass beads 60. Also placed with container 44 is a predetermined amount of gas, such as air, indicated at 62. The quantity of gas provided within container 44 is such as to cause the gas to expand, upon the creation of a vacuum in chamber 12, and permit only approximately one half of container 44 to fill with blood.

In operation, an empty flexible container 44, including glass beads 60 and gas 62 provided therein, is positioned within inner chamber 32. The blood collection line 45 is extended through opening 28 and the lid 16 is lowered to its closed position. The blood collection line 45 is then clamped off outside outer chamber 12. A vacuum is drawn in outer chamber 12 through a vacuum line (not shown) which is connected to fitting 26 in a conventional manner. As the vacuum is being drawn in chamber 12 the bladder 48 is caused to expand due to the fact that it is vented to atmosphere through line 50. The resultant expansion of bladder 48 exerts pressure on the two halves of inner chamber 32 causing them to pivot into contact with each other to attain its closed position. The vacuum created within outer chamber 12 is also effective to expand the gas 62 within container 44.

To collect blood from either a human donor or an animal, a phlebotomy is performed with the terminal end of blood collection line 45. Upon removal of the clamp from line 45, the negative pressure, created by the vacuum in outer chamber 12, against the walls of container 44 will cause it to expand and blood to be drawn into the container. During the collection of the blood the apparatus 10 is continuously agitated causing the beads 60 to move through the blood and whip out the fibrin. The blood continues to flow into container 44 until the back pressure of the expanded gas 62 creates sufficient pressure to stop the flow of blood. The collection line 45 is then clamped off.

If inner chamber 32 is properly sized and the proper initial quantity of gas 62 is provided in container 44, the result will be a flexible container 44 which has become rigid within inner chamber 32 having been filled approximately half with the collected blood and half with the beads 60 and the expanded gas 62. In this condition it can be readily appreciated that due to the headroom created by the gas pocket 62 and the rigidity of the container 44 within the chamber 32, by continuing the application of an agitating motion thereto the glass beads 60 are able to move rapidly through the blood and continue to whip out the fibrin. After defibrination is completed the vacuum within chamber 12 is released by stopping the vacuum drawn through fitting 26 and opening lid 16. The venting of outer chamber 12 to atmosphere causes the bladder 48 to deflate, which in turn causes the inner chamber 32 to split apart into its open position. The venting of chamber 12 is also effective to return the gas 62 within container 44 to its original volume. The container 44 being about half full of blood, and still containing the glass beads 60 and gas 62, which would otherwise be difficult to remove, may be easily removed from the inner chamber 32 because it is no longer exerting pressure against the walls of chamber 32.

After the container 44 is removed from chamber 32, the blood collected therein is typically transferred to a holding container (not shown). During such transfer the blood is directed through an auxiliary line 65, associated with container 44, and a filter 68, in communication therewith, for filtering out the fibrin which had previously been separated out of the blood.

Referring to FIG. 2, an alternative blood collecting container 44' is shown of substantially identical construction as container 44 shown in FIG. 1. The only difference is that a reticulated, fully open pore, foam material 60' is substituted for the beads 60. Foam material 60' is characterized by a three-dimensional skeletal structure of strands having a very high degree of permeability. In its preferred form the foam material 60' occupies a substantial portion of the volume of container 44' and is preferably secured to the bottom thereof. A presently preferred foam material 60' is manufactured by the Scott Paper Company and designated as "Scott Industrial Foam." This material is manufactured in various pore sizes between 7 and 100 pores per linear inch. The present invention contemplates the use of such material in the 7 to 30 pores per linear inch range and preferably about 10 pores per linear inch.

In operation, the container 44' is merely substituted for the container 44 and the procedure as hereinabove described is followed. However, with the use of container 44', instead of making use of the movement of the beads 60 through the blood to whip out the fibrin, the movement of the blood through the openings or pores in reticulated material 60' causes the fibrin to attach to the surfaces of the skeletal structures of material 60'. After completion of the entire procedure as recited hereinabove, it is anticipated that the container 44' will be disposed of and not be reused.

It should be pointed out that the present invention contemplates the use of numerous other alternative reticulated materials than that specifically mentioned above. Such materials need only have a similar porosity as the above foam material and be able to meet the requirements of operating in such a medical environment. The choice of the specific material is not deemed a critical part of the present invention.

This invention is not to be limited by the embodiments shown in the drawings and described in the description, which are given by way of example and not of limitation, but only in accordance with the scope of the appended claims.

What is claimed is:

1. A method of collecting and defibrinating blood in a flexible container, comprising the steps of:
   (a) adding and confining a predetermined quantity of gas and a plurality of small formed elements within the flexible container;
   (b) positioning the flexible container within a vacuum chamber;
   (c) creating a vacuum within the chamber which in turn causes the confined gas within the flexible container to expand and create a gas pocket therein;
   (d) collecting the blood into the flexible container such that the gas pocket and collected blood substantially fill and rigidize the flexible container; and
   (e) agitating the flexible container so as to cause the formed elements to move rapidly through the blood and the gas pocket and whip out the fibrin.

2. A method of collecting and defibrinating blood in a flexible container, comprising the steps of:
   (a) adding and confining a predetermined quantity of gas and a reticulated material within the flexible container;
   (b) positioning the flexible container within a vacuum chamber;
   (c) creating a vacuum within the chamber which in turn causes the confined gas within the flexible container to expand and create a gas pocket therein;
   (d) collecting the blood into the flexible container such that the gas pocket and collected blood substantially fill and rigidize the flexible container; and
   (e) agitating the flexible container so as to cause the blood to move through the gas pocket and the reticulated material such that the fibrin attaches to the surfaces of the reticulated material.

3. A method of collecting and defibrinating blood in a flexible container, comprising the steps of:
   (a) confining a predetermined amount of gas and a plurality of small formed elements within the flexible container;
   (b) positioning the flexible container within an outer vacuum chamber;
   (c) confining the flexible container within an inner chamber having an open and closed position;
   (d) retaining the inner chamber in its closed position;
   (e) creating a vacuum within the outer chamber which in turn causes the gas within the flexible container to expand;
   (f) collecting the blood into the flexible container;
   (g) agitating the inner chamber so as to cause the formed elements to move rapidly through the blood and whip out the fibrin;
   (h) venting the outer chamber to atmosphere;
   (i) moving the inner chamber from its closed position to its open position; and
   (j) removing the flexible container from the inner chamber.

4. The method as defined in claim 3 including the step of directing the blood collected in the flexible container through a filter to remove the fibrin from the blood.

5. The method as defined in claim 4 wherein the creation of the vacuum within the outer chamber is effective to retain the inner chamber in its closed position and the venting of the outer chamber causes the inner chamber to move to its open position.

6. A method of collecting and defibrinating blood in a flexible container, comprising the steps of:
   (a) confining a predetermined amount of gas and a reticulated material within the flexible container;
   (b) positioning the flexible container within an outer vacuum chamber;
   (c) confining the flexible container within an inner chamber having an open and closed position;
   (d) retaining the inner chamber in its closed position;
   (e) creating a vacuum within the outer chamber which in turn causes the gas within the flexible container to expand;
   (f) collecting the blood into the flexible container;
   (g) agitating the inner chamber so as to cause the blood to move rapidly through the reticulated material such that the fibrin attaches to the surfaces of the reticulated material;
   (h) venting the outer chamber to atmosphere;
   (i) moving the inner chamber from its closed position to its open position; and
   (j) removing the flexible container from the inner chamber.

7. The method as defined in claim 6 including the step of directing the blood collected in the flexible container through a filter to remove the fibrin from the blood.

8. The method as defined in claim 7 wherein the creation of the vacuum within the outer chamber is effective to retain the inner chamber in its closed position and the venting of the outer chamber causes the inner chamber to move to its open position.

9. Apparatus for collecting and defibrinating blood in flexible containers, comprising:
   (a) a rigid outer chamber having a fluid inlet opening and a vacuum port;
   (b) a flexible container disposed within said outer chamber in communication with said fluid inlet for receipt of blood therein upon the creation of a vacuum within said outer chamber through said vacuum port;
   (c) inner chamber means disposed within said outer chamber for receipt of said flexible container therein, said inner chamber means being split into at least two sections which are movable between a closed position and an open position; and
   (d) means disposed within said outer chamber for retaining said inner chamber in its closed position as blood is being received into said flexible container;
   (e) said flexible container being defined by a flexible outer skin portion and includes a plurality of small solid masses and a predetermined quantity of gas contained therein, such that as a vacuum is drawn in said outer chamber the gas in said flexible container is caused to expand causing said flexible container to expand into contact with said inner chamber.

10. Apparatus for collecting and defibrinating blood in flexible containers, comprising:
(a) a rigid outer chamber having a fluid inlet opening and a vacuum port;
(b) a flexible container disposed within said outer chamber in communication with said fluid inlet for receipt of blood therein upon the creation of a vacuum within said outer chamber through said vacuum port;
(c) inner chamber means disposed within said outer chamber for receipt of said flexible container therein, said inner chamber means being split into at least two sections which are movable between a closed position and an open position; and
(d) means disposed within said outer chamber for retaining said inner chamber in its closed position as blood is being received into said flexible container;
(e) said flexible container being defined by a flexible outer skin portion and includes a reticulated material and a predetermined quantity of gas contained therein, such that as a vacuum is drawn in said outer chamber the gas in said flexible container is caused to expand causing said flexible container to expand into contact with said inner chamber.

* * * * *